United States Patent
Cadeddu et al.

(10) Patent No.: US 7,429,259 B2
(45) Date of Patent: Sep. 30, 2008

(54) SURGICAL ANCHOR AND SYSTEM

(76) Inventors: Jeffrey A. Cadeddu, 4929 Swiss Ave., Dallas, TX (US) 75214; Richard A. Bergs, 5809 Brookline Dr., Rowlett, TX (US) 75089; Raul Fernandez, 2103 Ridgedale Dr., Arlington, TX (US) 76013; Linda A. Baker, 707 Saratoga Dr., Southlake, TX (US) 76092

( * ) Notice: Subject to any disclaimer, the term of this patent is extended or adjusted under 35 U.S.C. 154(b) by 261 days.

(21) Appl. No.: 10/999,396

(22) Filed: Nov. 30, 2004

(65) Prior Publication Data

US 2005/0165449 A1 Jul. 28, 2005

Related U.S. Application Data

(60) Provisional application No. 60/536,765, filed on Jan. 15, 2004, provisional application No. 60/526,700, filed on Dec. 2, 2003.

(51) Int. Cl.
*A61B 17/00* (2006.01)
(52) U.S. Cl. .......................................................... 606/1
(58) Field of Classification Search ................. 128/898; 606/151–153
See application file for complete search history.

(56) References Cited

U.S. PATENT DOCUMENTS

| | | | | |
|---|---|---|---|---|
| 3,906,217 A * | 9/1975 | Lackore | ...................... | 362/396 |
| 5,333,624 A * | 8/1994 | Tovey | ......................... | 128/897 |
| 5,352,219 A | 10/1994 | Reddy | | |
| 5,445,615 A * | 8/1995 | Yoon | ....................... | 604/99.04 |
| 5,540,648 A * | 7/1996 | Yoon | ......................... | 600/114 |
| 5,704,900 A * | 1/1998 | Dobrovolny et al. | ........ | 600/229 |
| 5,944,298 A * | 8/1999 | Koike | ......................... | 248/674 |
| 6,524,283 B1 * | 2/2003 | Hopper et al. | .............. | 604/264 |
| 6,535,764 B2 * | 3/2003 | Imran et al. | ................... | 607/40 |
| 6,656,194 B1 * | 12/2003 | Gannoe et al. | .............. | 606/153 |
| 6,974,462 B2 * | 12/2005 | Sater | ........................... | 606/72 |
| 7,120,498 B2 * | 10/2006 | Imran et al. | ................... | 607/40 |
| 2002/0030148 A1 * | 3/2002 | Oddsen | ........................ | 248/314 |
| 2002/0095175 A1 * | 7/2002 | Brock et al. | .................. | 606/205 |
| 2002/0165589 A1 * | 11/2002 | Imran et al. | ................... | 607/40 |
| 2003/0066938 A1 * | 4/2003 | Zimmerman | ................ | 248/301 |
| 2003/0139758 A1 * | 7/2003 | Hopper et al. | .............. | 606/185 |
| 2004/0050395 A1 * | 3/2004 | Ueda et al. | .................. | 128/899 |
| 2005/0165449 A1 * | 7/2005 | Cadeddu et al. | ............. | 606/232 |

* cited by examiner

*Primary Examiner*—Henry M Johnson, III
(74) *Attorney, Agent, or Firm*—Edwin S. Flores; Chalker Flores LLP (57) ABSTRACT

The present invention is a device and system for manipulating a surgical tool at an intended location, e.g., a confined or inaccessible space, which includes a surgical anchor having at least one opening, wherein the opening provides a catch for a pin; and at least one anchor point to position and orient a surgical tool inside a human body. The apparatus and system of the present invention allows for the use of multiple intra-abdominal surgical tools inserted through a single incision.

15 Claims, 11 Drawing Sheets

SURGICAL ANCHOR AND SYSTEM

TECHNICAL FIELD OF THE INVENTION

The present invention relates to an apparatus and system for performing surgery, and in particular, to a surgical anchor for hands-free operation and control of medical instruments inside a body cavity.

BACKGROUND OF THE INVENTION

This application claims priority to U.S. Provisional Application Ser. No. 60/526,700, filed Dec. 2, 2003; and U.S. Provisional Application Ser. No. 60/536,765, filed Jan. 15, 2004. Without limiting the scope of the invention, its background is described with respect to surgical procedures, and in particular, laparoscopy.

Compared with open surgery, laparoscopy results in significantly less pain, faster convalescence and less morbidity. However, eye-hand dissociation, a two-dimensional field-of-view and fixed instrumentation with limited degrees of freedom contribute to a steep learning curve and demanding dexterity requirements for many laparoscopic procedures. One of the main limitations of laparoscopy is the fixed working envelope surrounding each trocar, often necessitating placement of multiple ports to accommodate changes in position of the instruments or laparoscope to improve visibility and efficiency. The placement of additional working ports contributes to post-operative pain and carries a small risk of bleeding or adjacent organ damage. What is needed is a system that reduced the required number of ports.

One such system is disclosed in U.S. Pat. No. 5,352,219, issued to Reddy. A two-part modular tool and method is taught for use in conjunction with laparoscopic techniques by enabling tools to be manipulated within a body cavity through holes created by a shank. The two-part tool has an instrument head initially inserted through a laparoscopic port and an acuminate shaft that intra-corporeally attaches to the instrument head. The instrument head is then manipulated through the needle hole at the site of desired use. The instrument head may be any tool configuration useful in surgical procedures that can be miniaturized to pass through a laparoscopic port. Problem associated with the invention are that the tool has a limited area of use, the tool is limited by the strength and length of the needle and the tool is limited to the site of insertion. The limited two and three dimensional field of view within the body cavity may cause insertion of the needle at the wrong location, requiring additional insertions of the shank, thereby increasing greatly the number of skin punctures and increased morbidity from multiple punctures. Furthermore, in order the manipulate the tool, the needle(s) must not only be of a diameter and strength to make the tool useful, without the benefit of a trocar the tool damages the lining at the site of puncture every time the tool is actuated.

SUMMARY OF THE INVENTION

In order to provide for greater flexibility of endoscopic viewing and instrument usage and to further reduce morbidity, a laparoscopic surgical anchor system has been developed around an internal platform capable of supporting various laparoscopic tools that is secured via a pin or needle to the abdominal wall. The pin is able to provide electrical, mechanical, pneumatic and other power or support externally to the surgical anchor located internally.

More particularly, the present invention includes a device for manipulating a surgical tool at an intended manipulation location, e.g., in a confined or inaccessible space wherein the surgical anchor has at least one opening that provides a catch for a pin and at least one anchor point for the surgical tool. The pin may be, e.g., a needle that is threaded, beaded, knotched and the like for insertion and self-locking into the catch at the opening in the surgical anchor. The pin may even provide electrical power, pneumatic power, communication or even light to the surgical tool attached to the surgical anchor.

Surgical tools for use with the present invention may be attached to the surgical anchor by a universal joint and may even be, e.g., completely or partially self-actuating, controlled manually or magentically. Every type of surgical tool that has been reduced in size for entry into a body cavity via a trocar may be attached to the surgical anchor, e.g., a camera, a retractor, a paddle, a hose, a cutting tool, a light, a hook, a net or an anchor provided the tool includes an attachment point to the surgical anchor. The surgical tool may also include a drawstring for removing the surgical tool. In one embodiment, the surgical anchor and the surgical tool are of unitary construction and inserted through a trocar at the same time, e.g., anchored surgical camera. The surgical anchor may be made of one or more materials, e.g., surgical plastic, stainless steel, aluminum, nylon, polyester, and mixtures and combinations thereof.

In another embodiment, the surgical anchor include at least one opening, wherein the opening provides a catch for a pin, at least one anchor point for a surgical tool and a ferrous material disposed in or about the surgical anchor. The ferrous material may be disposed on or about the surgical anchor or it may even be a wire, wires, a wire bundle and the like and may be, e.g., oriented along the length of the surgical anchor in one or more orientations. The ferrous material on the surgical anchor may be used to attract a magnet positioned externally from the surgical anchor (within a body cavity), wherein manipulation of the magnet directs movement of the anchor within the body cavity or vice verse, that is, the surgical anchor is magnetic and a ferrous material or another magnet is external to the body cavity. In one embodiment the magnet is, e.g., a permanent magnet.

Yet another embodiment of the present invention is a remotely operated surgical device that has a generally tubular anchor with at least one opening, wherein the opening provides a catch for a pin, at least one anchor point for a surgical device and a surgical device anchored to the anchor point of the anchor, wherein the surgical tool can operate independently of a hand-held laparoscopic tool within a confined space at distances greater than, e.g., 20 centimeters.

Yet another embodiment of the present invention is a general purpose surgical platform that includes an anchored surgical device (e.g., magnetically anchored) that has a linear ferrous portion that extends along at least one length of the surgical device and an intraabdominal tool anchor point, wherein the platform allows for hands-free operation within a limited surgical envelope. Generally, the magnetically anchored surgical device will collapse to a cylindrical diameter of between about 5, 8, 12 and about 15 mm for insertion through a trocar. The anchored surgical device may also include an opening with a catch for semi-permanent anchoring of the device. An intraabdominal tool may be attached prior to or after insertion of the platform into the body cavity at the surgical anchor point, wherein the intraabdominal tool is a camera, a retractor, a scissors, a paddle, a hose, a cutting tool, a light, a hook, a net and the like. The anchor may also include one or more suction cups for additional attachment strength.

The surgical anchor may further include a ferrous insert, coating or combination thereof that permits manipulation (position and orientation) of the anchor after insertion through a trocar internally without the need for permanent tools or connections. The surgical anchor may also include magnets or suction cups that increase the control for positioning and strength of attachment in a hands-free system. After insertion into, e.g., an abdominal cavity, the surgical anchor and tools attached thereto remain surgeon-controlled via, e.g., external magnetic couples on the patient's abdomen. Using the surgical system disclosed herein, instruments, e.g., miniature endoscopic cameras, lights, retractors, scalpels, and the like may be used to augment, e.g., the surgical field of view, surgical precision and anchoring.

Accordingly, the present inventors have recognized that the field of laparoscopic surgery needs a method and apparatus that enables a surgeon to manipulate the position and orientation of one or more instruments within a human body without the necessity for multiple trocars. To provide for greater flexibility of endoscopic viewing and instrument usage and to further reduce morbidity, the inventors have developed a novel laparoscopic system that allows for unrestricted intra-abdominal movement of an endoscopic camera and surgical instruments without additional port sites.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and, together with the detailed description of the invention, serve to explain the principles of the present invention.

DETAILED DESCRIPTION OF THE INVENTION

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

The description of laproscopic surgery is set forth to demonstrate the use of the present invention in one type of surgery and is not intended to be exhaustive or to limit the scope of the invention. Many modifications and variations are possible in light of the teachings described herein without departing from the spirit and scope of the following claims. It is contemplated that the use of the present invention can involve components having different characteristics. It is intended that the scope of the present invention be defined by the claims appended hereto, giving full cognizance to equivalents in all respects.

Surgical trocars are most commonly used in laparoscopic surgery. For example, prior to use of the trocar, the surgeon may introduce a Veress needle into the patient's abdominal cavity. The Veress needle has a stylet, which permits the introduction of gas into the abdominal cavity. After the Veress needle is properly inserted, it is connected to a gas source and the abdominal cavity is insufflated to an approximate abdominal pressure of, e.g., 15 mm Hg. By insufflating the abdominal cavity, pneumoperitoneum is created separating the wall of the body cavity from the internal organs.

A trocar with a piercing tip is then used to puncture the body cavity. The piercing tip or obturator of the trocar is inserted through the cannula or sheath and the cannula partially enters the body cavity through the incision made by the trocar. The obturator may then be removed from the cannula and an elongated endoscope or camera may be inserted through the cannula to view the body cavity, or surgical instruments may be inserted to perform ligations or other procedures.

A great deal of force is often required to cause the obturator to pierce the wall of the body cavity. When the piercing tip breaks through the cavity wall, resistance to penetration ceases and the tip may reach internal organs or blood vessels, with resultant lacerations and potentially serious injury. The creation of the pneumoperitoneum provides some free space within which the surgeon may stop the penetration of the trocar. To provide further protection, trocars have more recently been developed with spring loaded shields surrounding the piercing tip of the obturator. Once the piercing tip of the obturator has completely pierced the body cavity wall, the resistance of the tissue to the spring-loaded shield is reduced and the shield springs forward into the body cavity and covers the piercing tip. The shield thereby protects internal body organs and blood vessels from incidental contact with the piercing tip and resultant injury.

Once the cannula has been introduced into the opening in the body cavity wall, the pneumoperitoneum may be maintained by introducing gas into the abdominal cavity through the cannula. Various seals and valves have been used to allow abdominal pressure to be maintained in this fashion. Maintaining abdominal pressure is important both to allow working room in the body cavity for instruments introduced through the cannula and to provide free space for the puncturing of the body cavity wall by one or more additional trocars as may be required for some procedures.

A principal limitation of traditional laparoscopy relates to the fixed working envelope surrounding each trocar. These relatively small working envelopes often necessitate the placement of multiple ports in order to accommodate necessary changes in instrument position and to improve visibility and efficiency. The creation of additional ports is known to contribute to post-operative pain and to increase the risk of bleeding or organ damage. Therefore, the present invention has been developed to: (1) improve the control of tools within a surgical envelope; (2) reduce the number of trocars required (e.g., a single puncture); (3) improve the working envelope associated with, e.g., laproscopic surgery; and/or (4) improve instrument positioning, visibility and efficiency.

The present invention has been evaluated in a dry laboratory as well as in porcine models, with several others currently under investigation. Some of the anchoring designs disclosed herein have been optimized for size, strength and surgical compatibility, as well as the benefits, limitations and prospects for the use of incision-less, magnetically-coupled tooling in laparoscopic surgery are now being performed with the use of trocars and cannulas. Originally these devices were used for making a puncture and leaving a tube to drain fluids. As technology and surgical techniques have advanced, it is now possible to insert surgical instruments through the cannulas and perform invasive procedures through openings less than half an inch in diameter. These surgical procedures required previously incisions of many inches. By minimizing the incision, the stress and loss of blood suffered by a patient is reduced and the patient's recovery time is dramatically reduced.

The present invention is a platform capable of supporting one or more surgical tools that may are secured to the abdominal wall and subsequently positioned within the abdominal cavity through surgeon-controlled, e.g., using external magnetic couples on the patient's abdomen. Using the surgical anchor disclosed herein, in conjunction with the techniques outlined for magnetic manipulation, instruments such as miniature endoscopic cameras may be used to augment, e.g., the surgical field of view and surgical tools. The present inventors have evaluated the theoretical and empirical uses of anchoring designs optimized for size, strength and surgical compatibility, as well as the benefits, limitations and prospects for the use of incisionless, magnetically-coupled tooling in laparoscopic surgery.

One such system is a magnetic anchoring system design. Several types and generations of magnetic anchoring schemes have been developed and evaluated. A fundamental design decision arises in generating the magnetic field electrically or via permanently magnetized materials. Electromagnets were initially favored due to: (1) the intrinsic ability to control the field strength, from zero to a maximum desired value; and (2) high magnetizing forces available in a relatively small footprint. Ex vivo and in vivo studies were used to evaluate the attractive force needed for use of electromagnets and permanent magnets. With electromagnets it was found that field strength was high at direct contact with the core, however, the field strength across tissue dropped-off drastically over relatively short distances, resulting in relatively bulky and heavy devices even after optimizing their length-to-diameter ratio and winding configuration. It was also found that heating caused by resistance limited the useful force attainable from an electromagnet due to its effect on skin contact temperature, winding insulation integrity, and surgeon comfort; these drawbacks may be overcome with active cooling. Given these constraints, permanent magnets were also investigated and they were found to deliver a higher coupling force per unit volume than the basic electromagnetic designs, and they can be controlled, when required, by adjusting their distance from their magnetic couple manually or in a closed-loop system. One limitation of permanent magnets relative to electromagnets is that the coupling force is always present, causing attraction to unintended targets and thus requiring strict handling procedures in the operating room. As such, in some applications electromagnets may be preferred, while in others permanent magnets may be preferred.

Magnetic performance is the result of complex, three-dimensional field interactions governed by material, size, shape, location of magnetic poles, and location relative to the target. For this reason, practical design analyses and optimization are tractable only through computer simulation and empirical testing. In a transabdominal magnetic anchoring system design it was found that the coupling force between two magnets as a function of distance. A baseline analytic relationship is given by:

$$F = \frac{B^2 A}{8\pi} \quad (1)$$

where F is the attractive force in dynes, B is the flux density in gauss, and A is the gap cross-sectional area in cm². In the simplest case of interest, a pair of identical opposing cylindrical magnets of radius R, length L, and separated by an air gap G, the flux density at the gap center is approximated by:

$$B = B_r \left[ \frac{L + \frac{G}{2}}{\sqrt{R^2 + \left(L + \frac{G}{2}\right)^2}} - \frac{\frac{G}{2}}{\sqrt{R^2 + \left(\frac{G}{2}\right)^2}} \right] \quad (2)$$

where $B_r$, the residual flux density, is a material property.

The resulting force vs. gap characteristic resembled an inverse power relationship. In arriving at an optimal magnetic anchoring system configuration, the main constraint is the size of the intraabdominal couple; e.g., it was designed to fit through a standard 12 or 15 mm trocar port in conjunction with its attached tooling. The dimensions of the external anchor are not critical but must be kept as small as practical and ergonomically compatible with abdominal laparoscopic surgery. Lastly, the device will produce generally an appropriate coupling force, nominally higher than 500 grams at a 10 mm gap to be useful. These parameters have led to two different magnetic anchoring system embodiments, based on a ⌀9×12 mm internal magnet coupled to a ⌀25×50 mm external magnet in single-stack and double stack (side-by-side, 25 mm between centerlines) configurations; all use NdFeB rare-earth magnets.

The surgical anchor described herein may be used as a general purpose platform to which a variety of intraabdominal tools can be attached as well as externally positioned by the surgeon. One design constraint for these tools is that they must collapse to a cylindrical envelope 12 to 15 mm in diameter for insertion through the trocar; this is typically accomplished through pin joints which also allow for relative link motion when coupled to two external anchors. The tools that may be anchored to the surgical anchor may also be capable of self-actuation, e.g., self-actuating scissors, graspers, hook cautery, and fine-scan motion cameras. Unlike the recent generation of laparoscopic surgical robots, however, these instruments neither require, nor are limited, by the standard working envelope of a dedicated trocar port.

Figure 1A:
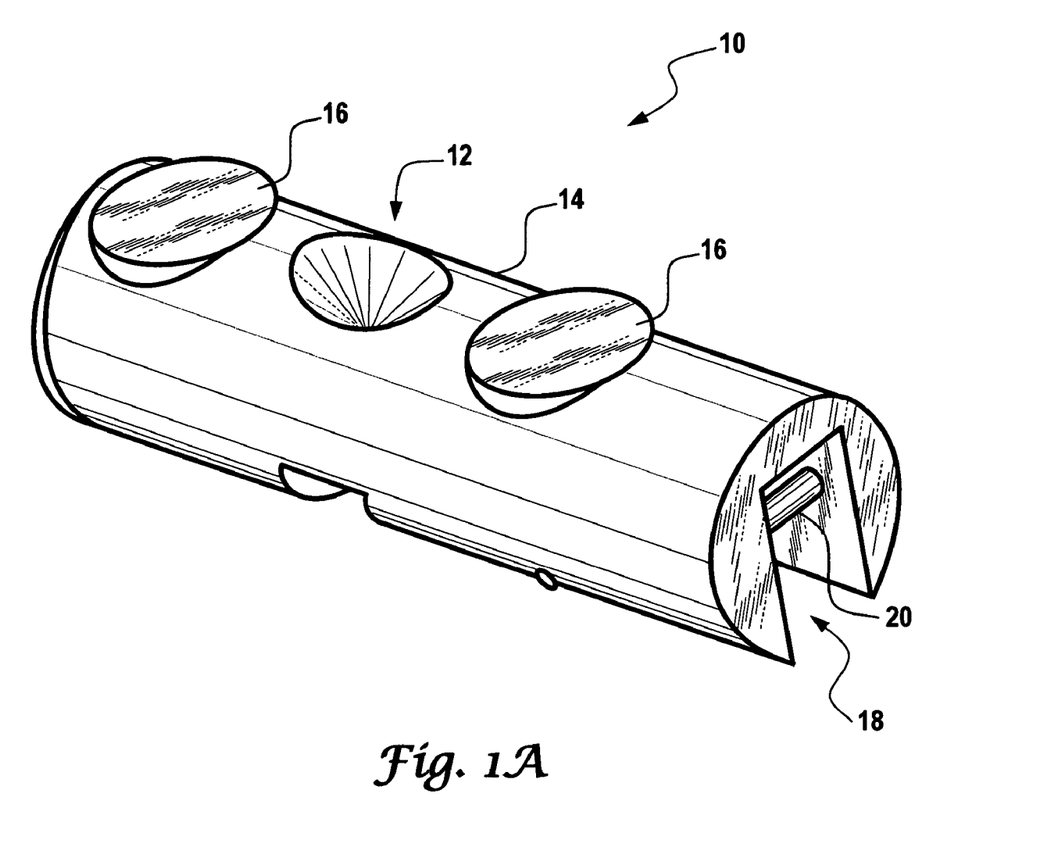
FIG. 1A is an isometric view, and 1B, 1C are cross-sectional views of the surgical anchor of the present invention.

FIG. 1A is an isometric view of one embodiment of the surgical anchor 10 of the present invention. The surgical anchor 10 depicted incorporates an opening 12 depicted having a conical shape within top surface 14 and having a conical focal point at the bottom of the opening 12 through which a pin (not depicted) is inserted to anchor the surgical anchor 10 to a surface. Also depicted are two pads 16 that, in this embodiment, are generally round and are inserted into the top surface 14 of the surgical anchor 10. Pads 16 may be made from, e.g., a ferrous material, coated with teflon or even a magnetic material. In one example, the pads 16 may be a ferrous, ferromagnetic, a magnetic material or combinations thereof that provide for external magnetic positioning and control of the surgical anchor 10 within a body lumen, e.g., the peritoneal cavity after insertion through a trocar. In this view, at least one anchor point 18 is depicted for holding a surgical tool (not depicted). The anchoring mechanism of the anchor point 18 may be integral with the surgical anchor 10, however, in this embodiment is depicted with a cotter pin 20 to which a wide variety of surgical tools may be attached.

Figure 1B:
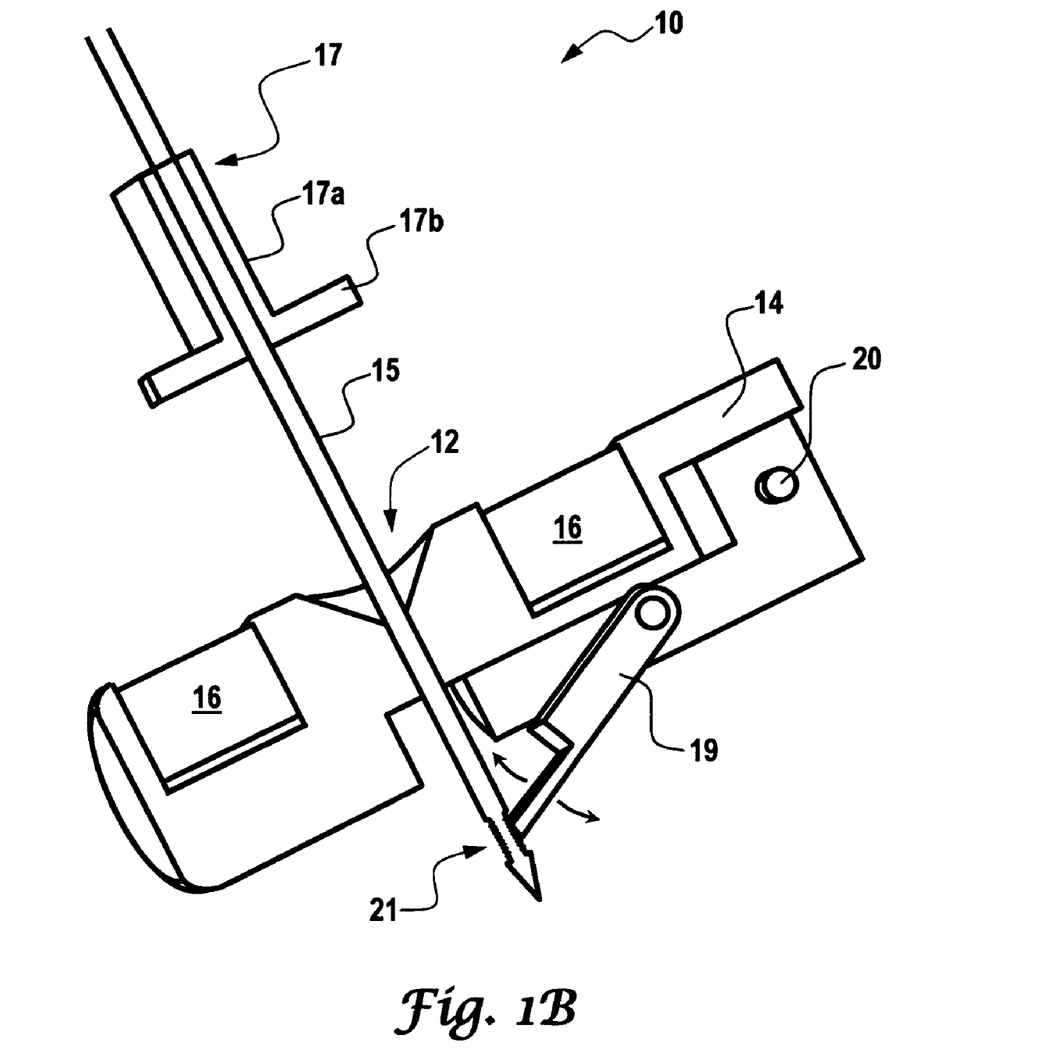
Figure 1C:
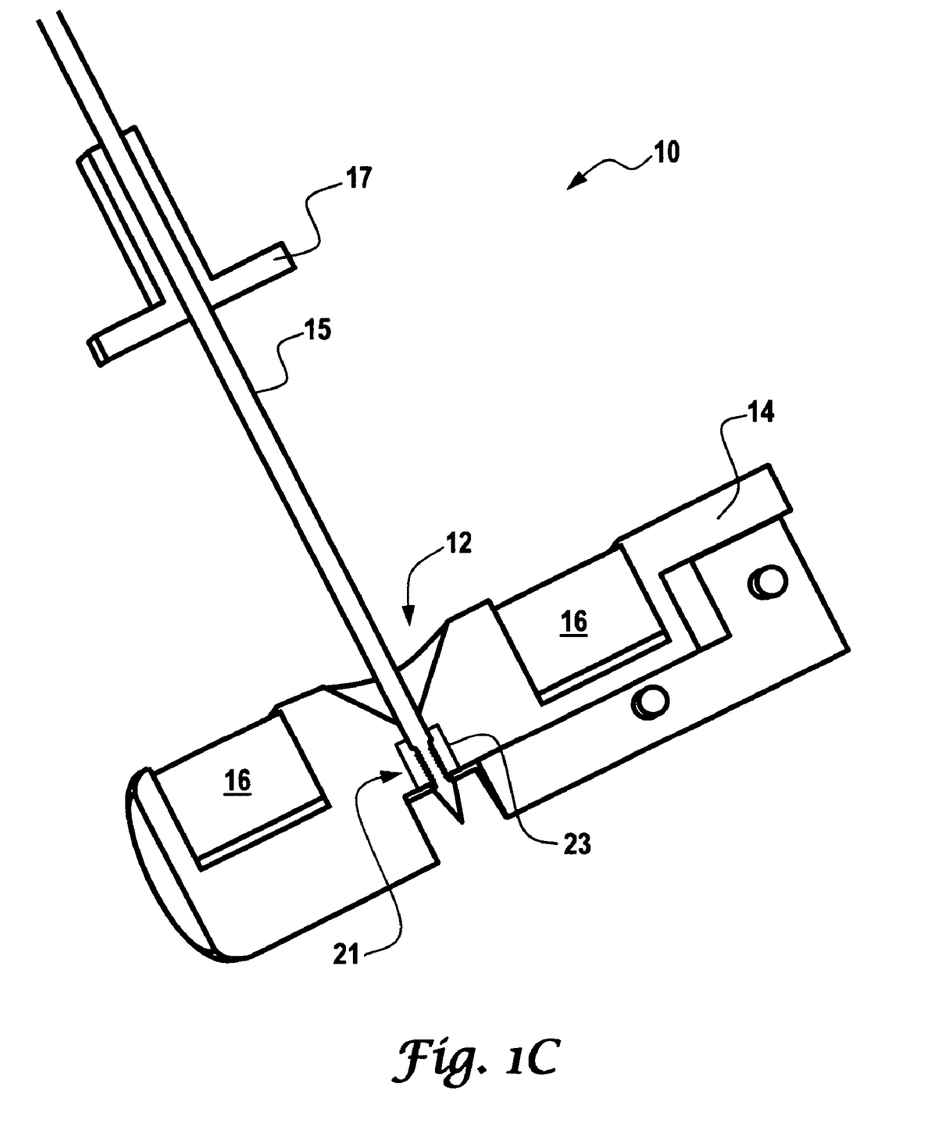

FIGS. 1B and 1C are cross-sectional view of surgical anchor 10 of the present invention in which two types of locking mechanisms for the pin 15 having a pin lock 17. The pin 15 will generally have a sharpened point for traversing a tissue. To hold the pin 15 in place, a pin lock 17, in this embodiment depicted as having a shaft 17a and a lock pad 17b is depicted. As with the surgical anchor 10 depicted in FIG. 1A, the surgical anchor of FIG. 1B includes as opening 12 having a conical focal point at the bottom of the opening 12 through which the pin 15 is inserted to anchor the surgical anchor 10, and having a locking arm 19 that self-locks. The pin 15 depicted has serrations 21, which may be used to increase friction and thereby improve the anchoring capacity of the surgical anchor 10. FIG. 1C depicts another variation of a locking mechanism for the pin 15 and surgical anchor 12 in which the serrations 21 thread into an internal thread 23. When using the surgical anchors 10 depicted in FIGS. 1B and 1C, the surgeon position the surgical anchor 10 as the anchor site and then may lock the anchor into position semi-permanently by inserting the pin 15 into the self-locking mechanism.

In traditional forms of laparoscopic surgery, laparoscopic instruments inserted into a body cavity are manipulated principally by the application of force to the portion of the laparoscopic instrument protruding from the patient and integral with a handle. The handle is controlled by the surgeon and requires at all times insertion through a trocar, e.g., a 5, 8, 10, 12 or even a 15 mm ID (internal diameter) trocar. Although this method is useful for adjusting the depth of insertion of the laparoscopic instrument and can provide a limited range of angular or side-to-side movement, all but minor changes in the orientation of the laparoscopic instrument may be accomplished without the creation of additional incisions in the patient.

The surgical anchor 10 of the present invention provides several distinct advantages over the use of conventional hand-held laproscopic tools. First, it provides an independent anchor point for the attachment of one or more surgical tools, retractors, scalpels, cameras, lights and the like that are inserted once into the patient through a single trocar. The independent surgical anchor 10 is anchored to the lumen of the body cavity by insertion of a single small pin, which may attached via, e.g., a self-locking mechanism, thereby providing a hands-free anchor point for other tools while also freeing-up the trocar for insertion of additional anchors or providing for insertion of another working surgical tool. Second, one or more independent surgical anchors may be inserted and tools may be swapped between the anchors without the need for additional large incisions. Third, by using magnetic positioning, the same surgical anchor may be moved from location to location, again reducing the number of major incisions while allowing maximum flexibility for tool use and positioning.

Figure 2A:
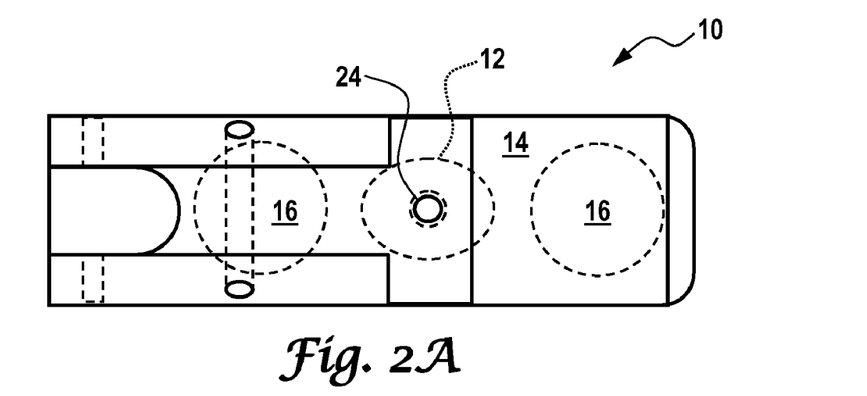
FIGS. 2A, 2B and 2C are a bottom, side and top view of a surgical anchor, respectively.

FIG. 2A is a bottom view of the surgical tool 10 that depicts a single anchor-point opening 11 in relation to the pads 16 and the opening 12. A self-locking ring 24 is depicted at the focal point of the opening 12. The self-locking ring 24 may easily be replaced with a screw (internal or external), a bolt or other fastener for a pin. In one embodiment, the entire structure of the surgical tool may be a plastic or ferrous material.

Figure 2B:
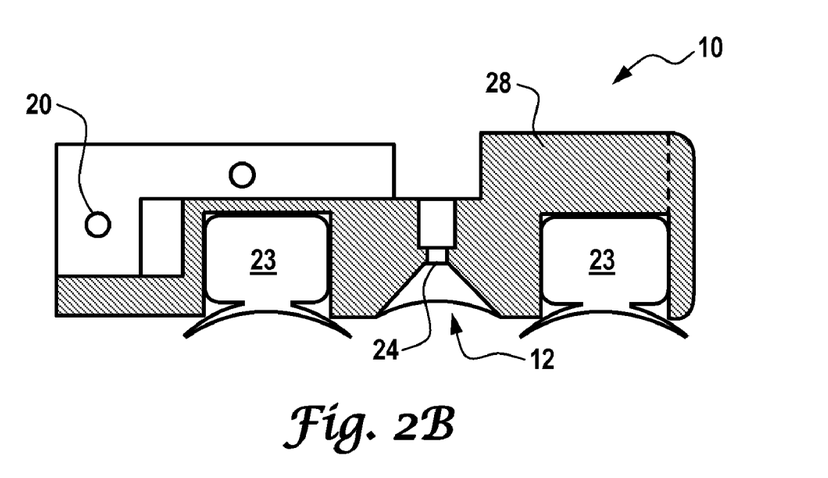

FIG. 2B is a cross-section of the surgical tool 10 that depicts the relationship between the opening 12, pad openings 16, and the cotter pin 20. In this cross-sectional view the surgical anchor 10 is depicted as top and a bottom components (26, 28), however, the surgical anchor 10 may be of unitary construction using, e.g., molding, milling and the like. The opening 12 is depicted as having generally a conical shape, however, any number of shapes or combination of shapes may be used for the opening, e.g., a circular and/or conical shape having a 135 degree internal angle may be used for pin insertion. Suction cups 23 are depicted in openings 26.

Figure 2C:
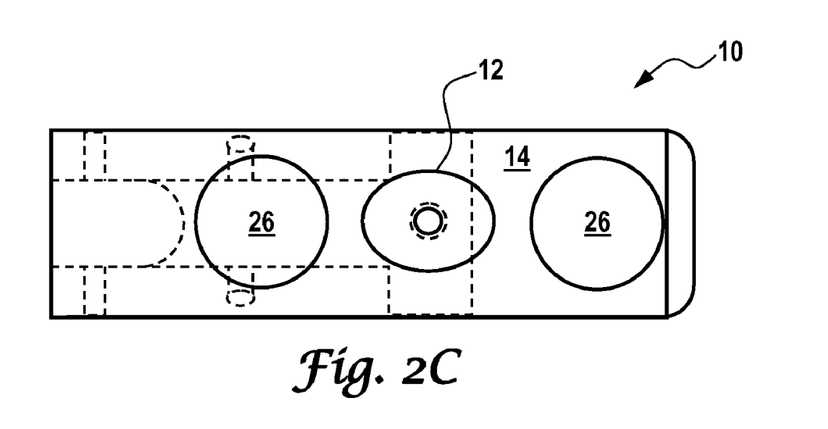

FIG. 2C is a top of the surgical anchor 10 that depicts two pad openings 26 in relation to the opening 12 on top surface 14. As will be apparent from the current disclosure, additional openings 12 and pad openings 26 may be added and positioned in a linear, parallel, square, oval, round, and/or in two and three-dimensions. The surgical anchor 10 shown in FIG. 1 is positioned in place by manual manipulation, or may be positioned with the help of, e.g., a magnetic field.

Figure 3:
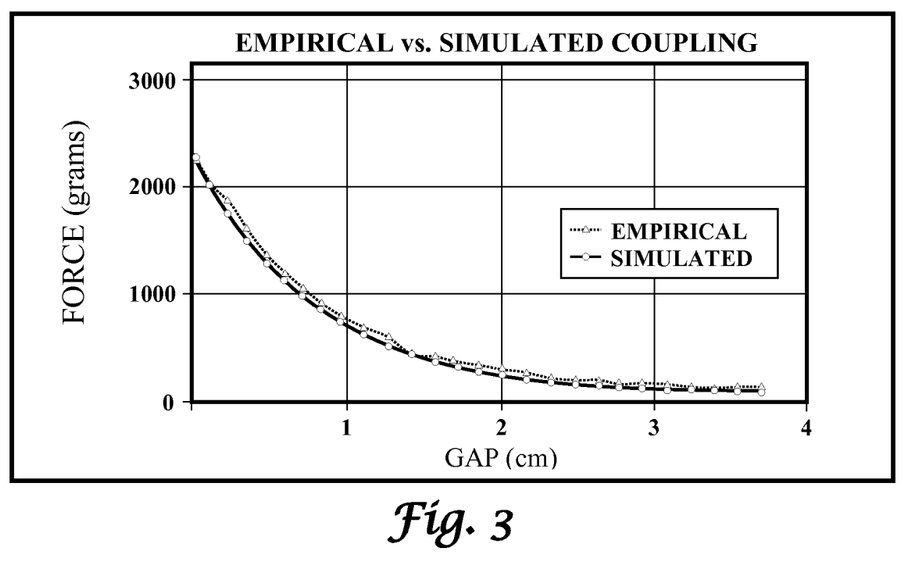
FIG. 3 is a graph of simulated and empirical force versus gap results using magnets for controlling the positioning of a surgical anchor.
Figure 4:
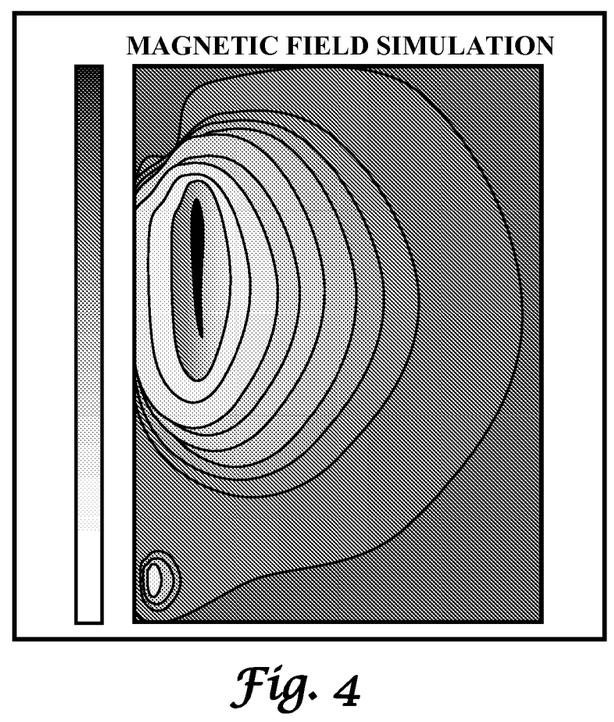
FIG. 4 is a magnetic field simulation for computer generated flux paths for a single-stack magnet configuration.

FIG. 3 shows the empirical versus simulated coupling force of a magnetic field. FIG. 3 shows the force (in grams) versus gap data. FIG. 4 is a magnetic field simulation of the magnetic flux paths for a single-stack magnet configuration. In certain embodiments, the magnets may be permanent magnets generating a magnetic field of a constant strength. In other embodiments, the magnetic field may be an electromagnetic field having a constant strength, a variable strength, or a varying time-dependent strength. Magnetic fields for use with the present invention may be single magnetic sources, or may be composed of arrays of smaller sources. In one embodiment, the pads 16 are magnetic pads that are attracted to a ferrous material external to the lumen, e.g., a single attachment point on a stand, a wire or even a three-dimensional cover that is positioned over the surgical subject or patient. In yet another embodiment, both the surgical anchor 12 and the external positioning and/or attachment point are magnetic.

Surgical tools for use with the present invention will generally be sized to be passable through a trocar port by a laparoscopic grasper or forceps for attachment to the surgical anchor 10. In some cases, it may be desirable for the surgical tools to be a camera, a camera with one or more lights (e.g., optic fibers), surgical retractors, e.g., a retractor, a sling retractor, a paddle retractor, a basket, a bag, a hook and the like, a cutting tool, e.g., a laser or a scalpel, or even a suction tube for removal of tissue. The surgical tool will include a hook or other locking mechanism that is complementary with the anchor point 18. The surgical anchor 10, the surgical tools, etc. may be formed of metal, plastic, combination of metal and plastics or other suitable material. The surgical tool may also include drawstrings to help remove the surgical tool through the trocar or other opening after use.

In one specific example, the surgical tool that is anchored to the abdominal lumen may be a high-resolution charge-coupled device (CCD) camera or even an analog camera. While the camera may obtain and transmit a signal independent of an external power source, the surgical anchor of the present invention may also provide electrical and optical contacts with the surgical tool attached to the surgical anchor. For example, a camera and lights may obtain, e.g., electrical power from the pin and be grounded via the patient or a wire within the pin. If the pin is made of, or includes, optic fiber, a signal may be transmitted to and from the camera through the pin itself. The pin may even provide electrical, mechanical, pneumatic, communications and the like to the surgical tool via or around the surgical anchor. In another embodiment, the camera delivers a signal via a radio frequency or other transmission system and is wireless.

The sensitivity, reliability and simplicity of operation of the system may be evaluated by direct comparison to conventional images captured using conventional laparoscopic instruments. Other image capture systems may be used in conjunction with the imaging system. For example, fiber optic leads may be placed close to the image and the image transferred for capture outside the body. In addition, wavelengths outside visible light may be captured by the imaging system.

Figure 5A:
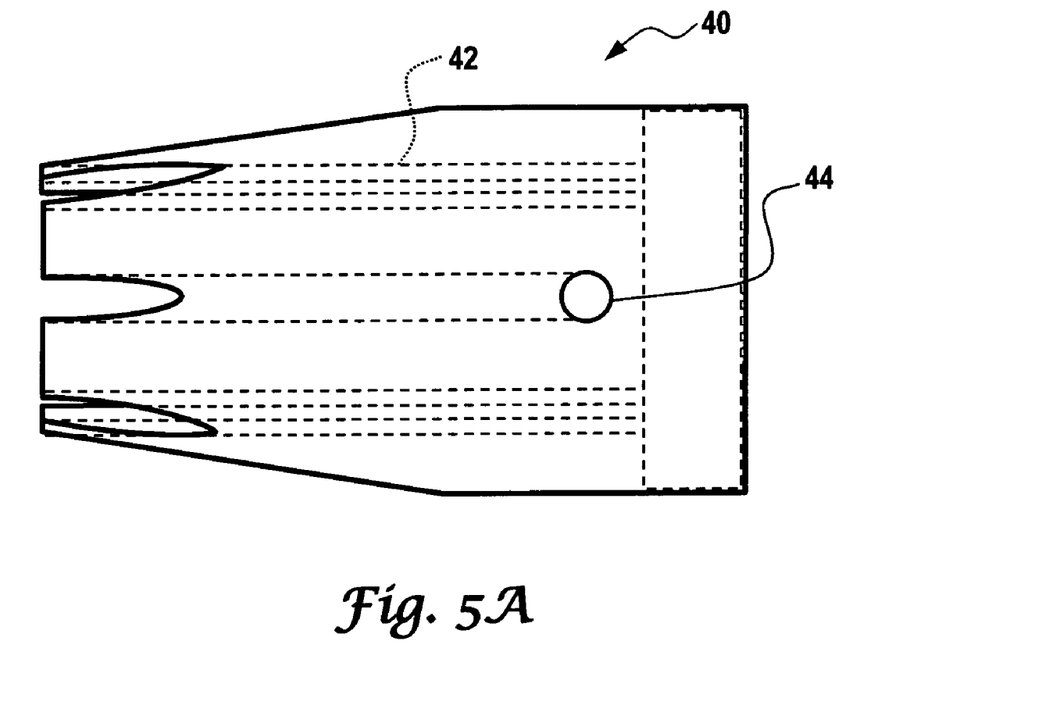
FIGS. 5A and 5B are a side and a bottom view, respectively, of a trocar cable and light port for use with the present invention, respectively.
Figure 5B:
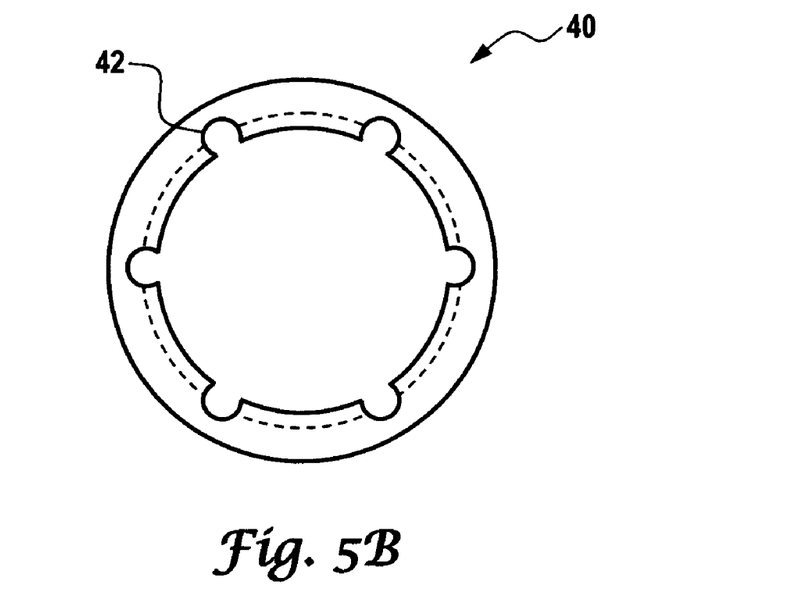

FIGS. 5A and 5B are a side and a bottom view of a trocar cable and light port 40, respectively, that may be used in conjunction with the present invention. Typically, light is required for any video system to transmit a signal for use in surgery. The trocar cable and light port 40 permits for the insertion of additional wires, optical fiber and pneumatic lines into, e.g., the abdominal area to provide command, control and electrical connections through the abdominal wall without leaking gas out of the abdomen. The trocar cable and light port 40 has one or more internal conduits 42 that traverse the length of the trocar cable and light port 40 and through which one or more cables, optic fiber and pneumatic lines may be inserted into the patient, while at the same time maintaining access to the intraabdominal cavity through the trocar. When not in use, the conduits 42 may be plugged at one or both ends or may even include a gel or gel-like materials that seals the conduit and thereby the trocar. Furthermore, the trocar cable and light port 40 depicted also includes a gas release opening 44 for introduction or release of gas from the intraabdominal or other cavity.

In conjunction with the surgical anchor 10, one or more conventional laproscopic tools may be inserted, positioned and used at the same time after introduction into the abdominal cavity through a single abdominal incision. Unlike conventional trocars which have a single smooth opening, the trocar cable and light port 40 allows the insertion of cables and a conventional laproscopic tool at the same time.

Figure 6A:
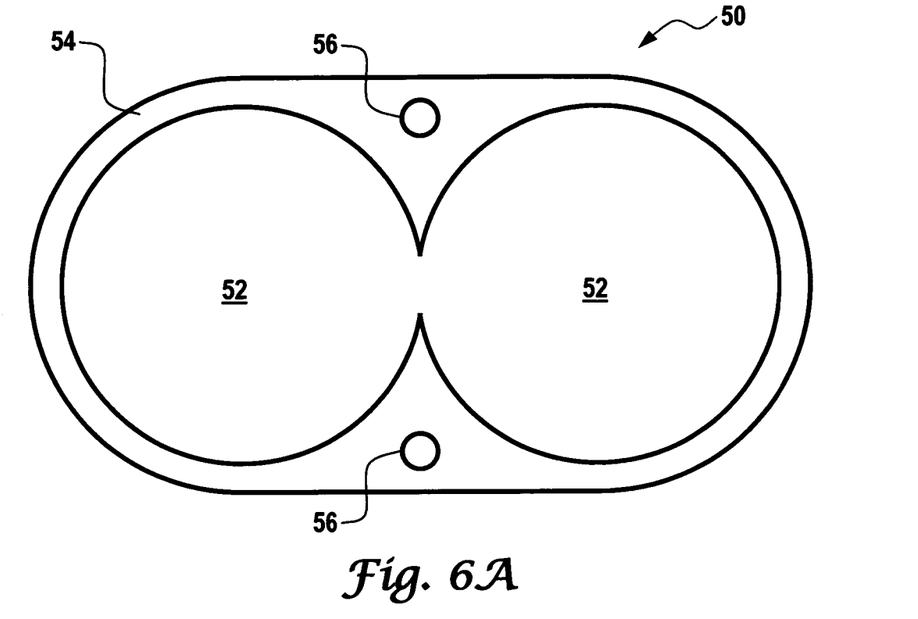
FIG. 6A is a top view of a dual-magnet, 6B is cross-sectional view of the dual magnet, and 6C is a cross-sectional view combining the surgical anchor and the dual magnet for use with the present invention.
Figure 6B:
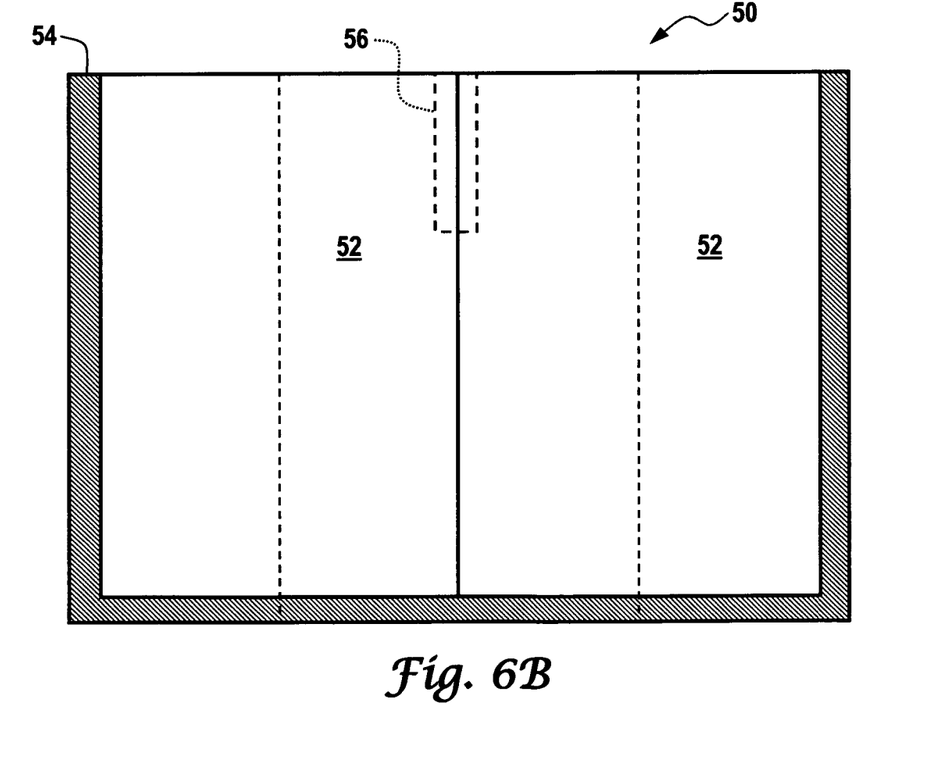

FIGS. 6A and 6B are a top and cross-sectional view, respectively, of a dual external magnet stack 50 for use with the surgical anchor when the surgical anchor is made of, or includes, a magnetically attracting material. The dual external magnet stack 50 has magnet openings 52 in casing 54 and will generally be small enough to be hand-held. Into each of the magnet opening 52 may be inserted a magnetic source in: N—S, S—N, S—S or N—N orientation. In one embodiment, the magnet is an electromagnet and the strength and orientation of the field may be externally controlled by providing power to the electromagnet. The magnet openings 52 are depicted as cylindrical, however, they may have any shape: oval, square, rectangular, etc. The holes 56 in the casing 54 and may be used to attach the dual external magnet stack 50 to a stand or holder. One particularly useful aspect of the dual external magnet stack 50 is that, when used in conjunction with the surgical anchor 10 depicted in FIG. 1 having pads 16, the dual external magnet stack 50 may be used to turn the surgical anchor 360 degrees while anchored by magnetically coupling the each of the magnets of the dual stack each to one of the pads 16.

Figure 6C:
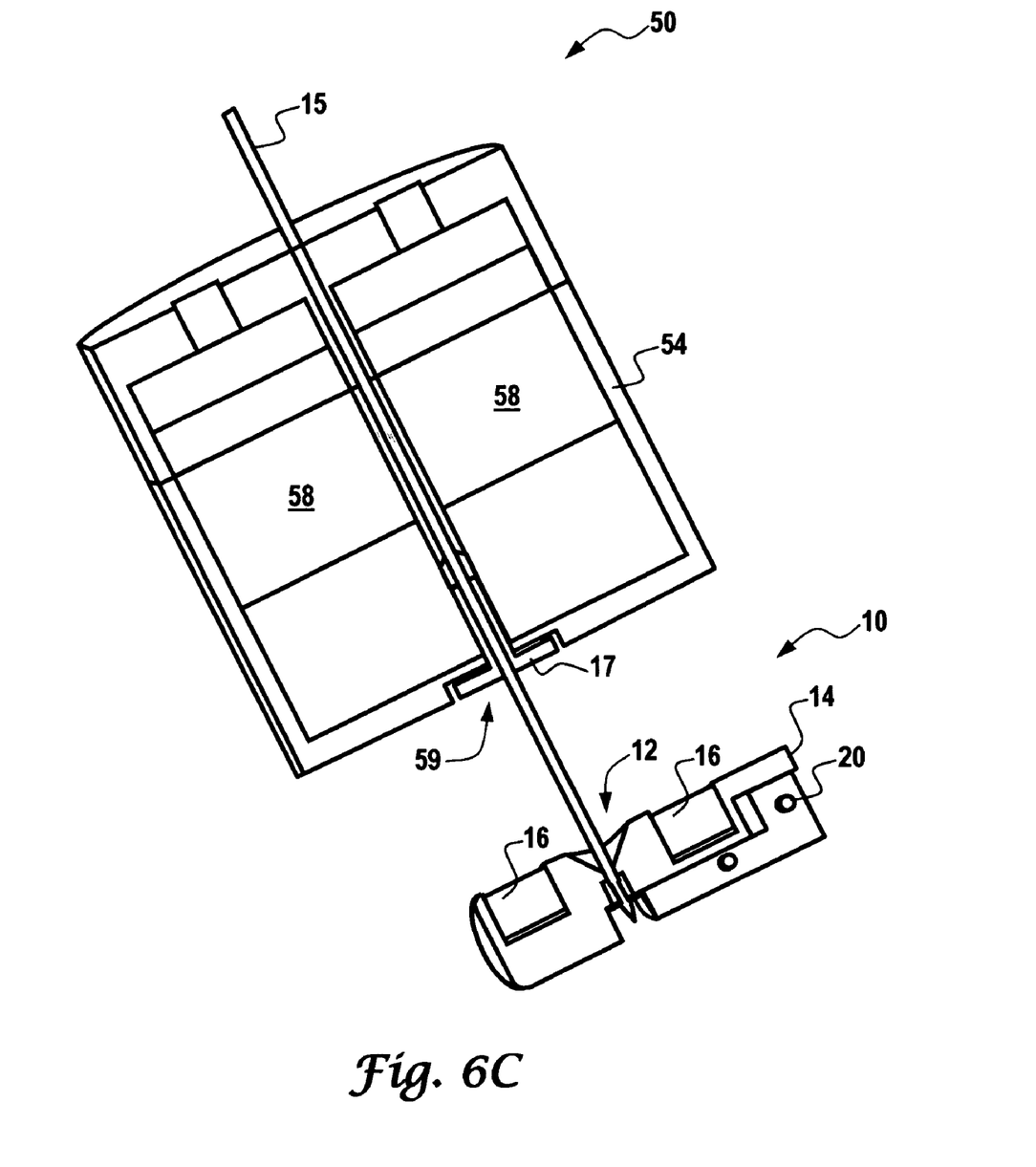

FIG. 6C combined the dual external magnet stack 50 has magnets 58 in the casing 54 in combination with the surgical anchor 10 depicted in FIG. 1A. The surgical anchor 20 is also shown in cross-section and with opening 12 through which the pin 15 is inserted to anchor the surgical anchor 10, and having a locking arm 19 that self-locks. The pin 15 then traverses the magnet stack 50, which includes within its casing 54 an opening 59 that has a internal opening into which the pin lock 17 is inserted and which may even permit the pin 15 to be locked into position with the magnet stack 50. By using the combination of the magnetic stack 50 with the pin 15 and the surgical anchor 10, the surgical anchor may even be rotated 360 degrees under the external control of the surgeon by rotating the magnet stack 50, which is magnetically connected with the surgical anchor when the pads 16 are of a magnetically attracting material.

A wide variety of permanent magnets may be used with the present invention, such as rare earth magnets, ceramic magnets, alnico magnets, which may be rigid, semi-rigid or flexible. Flexible magnets are made by impregnating a flexible material such as neoprene rubber, vinyl, nitrile, nylon or a plastic with a material such as iron having magnetic characteristics. Other examples of magnets for use as described hereinabove, are rare earth magnets include neodymium iron boron (NdFeB) and Samarium Cobalt (SmCo) classes of magnets. Within each of these classes are a number of different grades that have a wide range of properties and application requirements. Rare earth magnets are available in sintered as well as in bonded form.

Ceramic magnets are sintered permanent magnets composed of Barium Ferrite (BaO $(Fe_2O_3)_n$) or Strontium Ferrite (SnO$(Fe_2O_3)_n$), where n is a variable quantity of ferrite. Also known as anisotropic hexaferrites, this class of magnets is useful due to its good resistance to demagnetization and its low cost. While ceramic magnets tend to be hard and brittle, requiring special machining techniques, these magnets can be used in magnetic holding devices having very precise specifications or may be positioned within a protective cover, e.g., a plastic cover. Anisotropic grades are oriented during manufacturing, and must be magnetized in a specified direction. Ceramic magnets may also be isotropic, and are often more convenient due to their lower cost. Ceramic magnets are useful in a wide range of applications and can be pre-capped or formed for use with the present invention.

Figure 7:
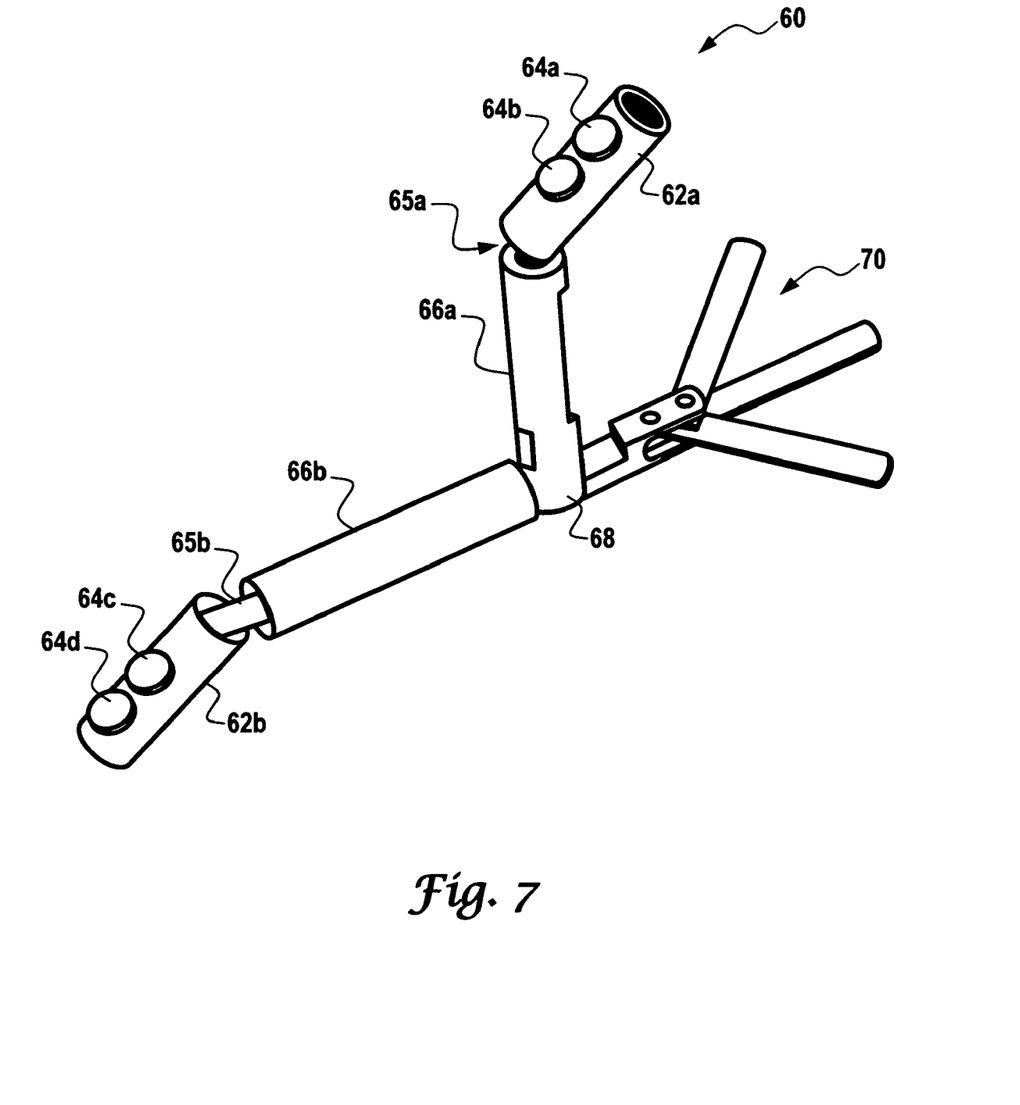
FIG. 7 is an isometric view of an anchored paddle retractor for use with the present invention.

FIG. 7 is an isometric view of one embodiment of an anchored tool 60. The anchored tool 60 has surgical anchors (62a, 62b) that may be individually anchored and/or controlled. In the embodiment depicted, magnets (64a, b, c and d) are depicted in the surgical anchors 62a, 62b for control and positioning via, e.g., the dual external magnet stack 50. In the anchored tool 60, the surgical anchors 62a, 62b are connected via universal joints (65a, 65b) to arms (66a, 66b), respectively, which are in turn connected to each other at joint 68. Connected to the joint 68 and under three dimensional control by the surgical anchors 62a, 62b via the arms 66a, 66b, is a tool 70, in this case depicted as a paddle retractor.

Figure 8:
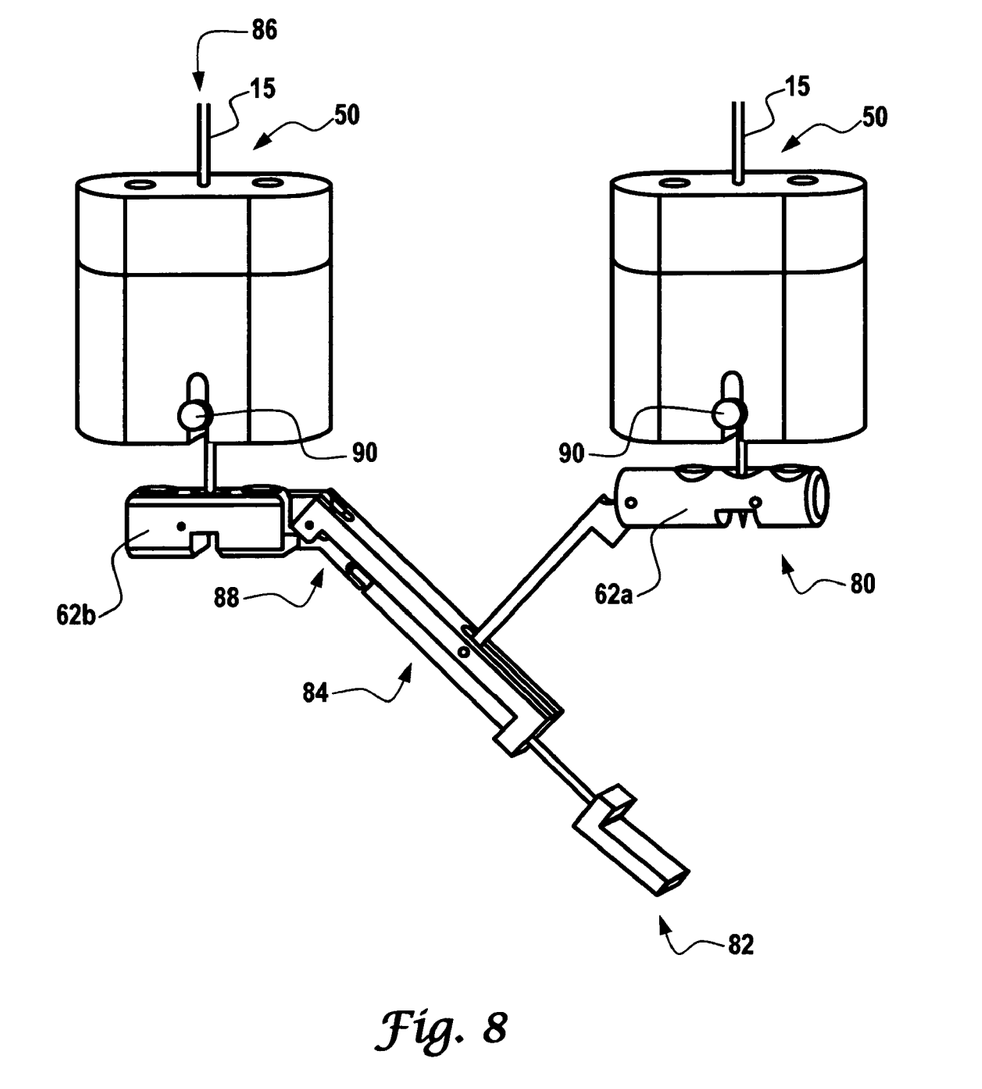
FIG. 8 is an isometric view of another embodiment of an anchored tool with a pneumatic piston.

FIG. 8 is an isometric view of another embodiment of an anchored tool 80 that includes, in this example, an actuated paddle retractor 82 and further includes a piston 84 that may be connected to a pneumatic source (not depicted) through an opening 86 in the pin 15. By providing pneumatic power from an external source through the opening 86 in pin 15 via a pneumatic connection 88 with the piston 84 to the paddle retractor 82, the surgeon is able to apply variable amounts of pressure at the desired time to the tool 80. The anchored tool 80 is depicted with two different embodiments of the surgical anchors 62a, 62b for control and positioning via the dual external magnet stack 50. In this embodiment, the magnet stack 50 is depicted with locks 90 that lock into position the pins 50 and which, as depicted, may be used to raise and lower the pins 15 in relation to anchors 62a, 62b via fine adjustments. An example of a lock 90 may be a self-locking or even a threaded lock that holds the pin via mechanical friction.

Figure 9:
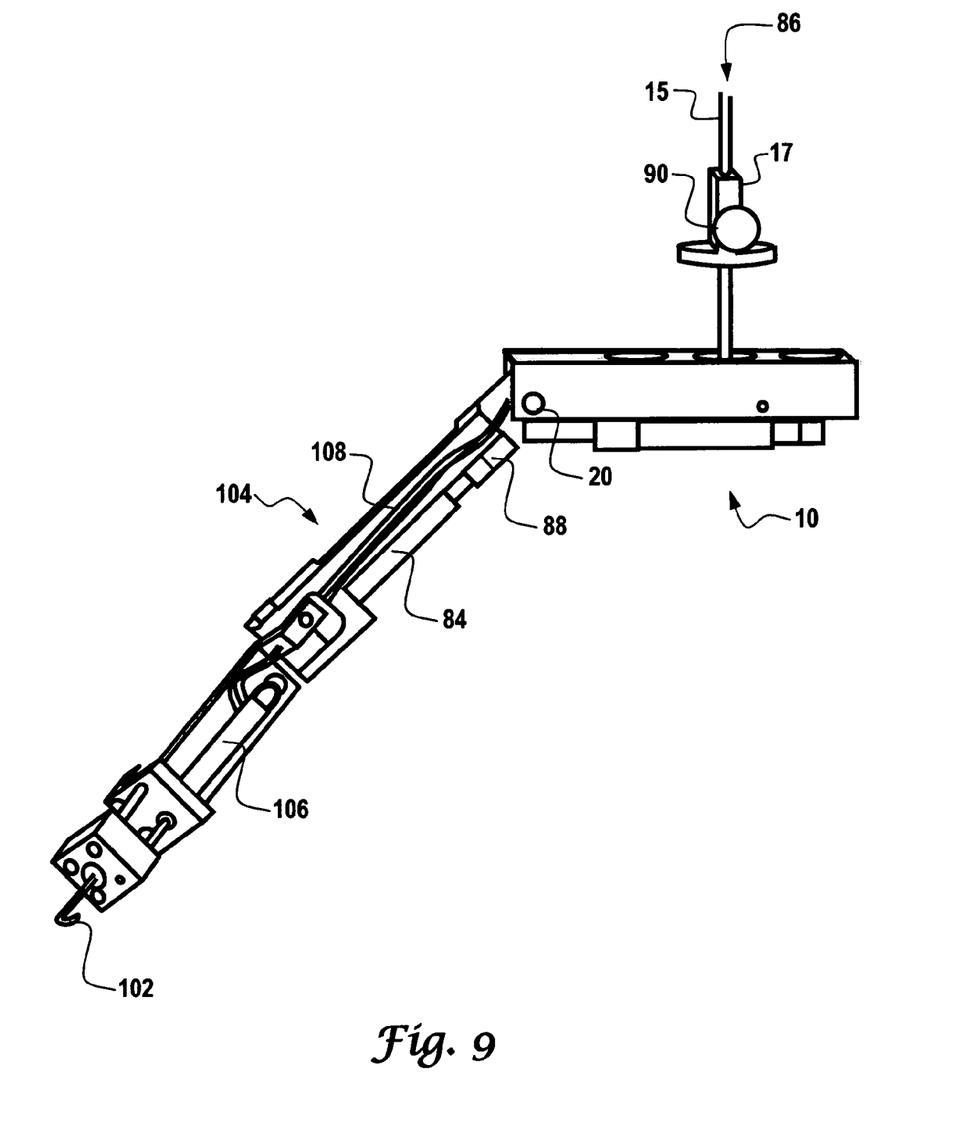
FIG. 9 is an isometric view of another embodiment of an anchored tool with both a pneumatic piston and an electrical actuator.

FIG. 9 is an isometric view of another embodiment of an anchored tool 100 that includes, in this example, a cutting hook 102 that is connected to an actuation arm 104 and further includes a piston 84 that may be connected to a pneumatic source via pneumatic connection 88 by pneumatic power provided through opening 86 in the pin 15. Also depicted in FIG. 9 is an electrical actuator 106 that is electrically connected to an external power source via wires 108 that electrically connect via the surgical anchor 10 with external electrical power provided via pin 15. By providing both electrical and pneumatic power from an external source through the pin 15, the surgeon is able to apply variable amounts of pressure at the desired time to the tool 80, provide for electrical and even computer control of the arm 104 and power to the hook cutting tool 102.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered. The description as set forth is not intended to be exhaustive or to limit the scope of the invention. Many modifications and variations are possible in light of the above teaching without departing from the spirit and scope of the following claims. It is contemplated that the use of the present invention can involve components having different characteristics. It is intended that the scope of the present invention be defined by the claims appended hereto, giving full cognizance to equivalents in all respects.

What is claimed is:

1. A magnetic surgical anchor system comprising:
an elongated member adapted for delivery via a trocar into a body cavity having a wall, the elongated member having a top surface and a bottom surface, at least one pad selected from one of a ferrous, ferromagnetic and magnetic materials inserted into the top surface, an opening for receiving and securing a pin, and an attachment member for attaching a surgical tool;
a pin adapted to engage the opening in the elongated member; and
an external casing comprising at least one magnetic stack, the casing adapted to allow magnetic cooperation with the elongated member when the elongated member is within the body cavity, the casing comprising a pin attachment channel, wherein the elongated member is positioned by movement of the casing external to the cavity and is secured by inserting the pin through the pin attachment channel through the cavity wall and into the opening in the elongated member.

2. The system of claim 1, wherein the elongated member has a diameter of between 12 and 15 mm.

3. The system of claim 1, wherein the opening of the elongated member comprises at least one of a catch, a self-locking catch or is threaded, for semi-permanent Anchoring of the pin to the elongated member.

4. The system of claim 1, further comprising a surgical tool selected from at least one of a camera, a retractor, a paddle, a hose, a cutting tool, a light, a hook or a net.

5. The system of claim 1, wherein the pin delivers at least one of electrical or pneumatic power to the surgical tool.

6. The system of claim 1, wherein the elongated member comprises at least one of surgical grade plastic, aluminum, titanium, stainless steel, nylon or polyester.

7. A magnetic surgical anchor system comprising:
an elongated member adapted for delivery via a trocar into a body cavity having a wall, the elongated member having a top surface and a bottom surface, at least one pad selected from one of a ferrous, ferromagnetic and magnetic materials inserted into the top surface, an opening for receiving and securing a pin, and a surgical tool;
a pin adapted to engage the opening in the elongated member; and
an external casing comprising at least one magnetic stack, the casing adapted to allow magnetic cooperation with the elongated member when the elongated member is within the body cavity, the casing comprising a pin attachment channel, wherein the elongated member is positioned by movement of the external casing to the cavity and is secured by attaching the pin to the channel, through the cavity wall and into the opening in the elongated member.

8. The system of claim 7, wherein the elongated member has a diameter of between 12 and 15 mm.

9. The system of claim 7, wherein the elongated member comprises at least one of surgical grade plastic, aluminum, titanium, stainless steel, nylon or polyester.

10. A magnetic surgical anchor system comprising:
an elongated member adapted for delivery via a trocar into a body cavity having a wall, the elongated member having a top surface and a bottom surface, at least one pad selected from one of a ferrous, ferromagnetic and magnetic materials inserted into the top surface, an opening for receiving and securing a pin, and a surgical tool;
a pin and pin lock wherein the pin lock is positioned in the opening of the elongated member and adapted to engage the pin; and
an external casing comprising at least one magnetic stack, the casing adapted to allow magnetic cooperation with the elongated member when the elongated member is within the body cavity, the casing comprising a pin attachment channel therethrough adapted to receive the pin and a channel pin lock, wherein the elongated member is positioned by movement of the casing external to the cavity and secured by inserting the pin through the channel in the casing, through the cavity wall and into the opening in the elongated member.

11. The system of claim 10, wherein the elongated member has a diameter of between 12 and 15 mm.

12. The system of claim 10, wherein the opening of the elongated member comprises at least one of a catch, a self-locking catch or is threaded for semi-permanent anchoring of the pin to the elongated member.

13. The system of claim 10, wherein the surgical tool comprises at least one of a camera, a retractor, a paddle, a hose, a cutting tool, n light, a hook or a net.

14. The system of claim 10, wherein the pin delivers at least one of electrical or pneumatic power to the surgical tool.

15. The system of claim 10, wherein the elongated member comprises at least one of surgical grade plastic, aluminum, titanium, stainless steel, nylon or polyester.

* * * * *